(12) United States Patent  
Ho

(10) Patent No.: US 9,345,849 B2  
(45) Date of Patent: May 24, 2016

(54) DEVICE AND METHOD FOR CAPTURING A SURFACE OF AN OBJECT

(71) Applicant: KONINKLIJKE PHILIPS N.V., Eindhoven (NL)

(72) Inventor: Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 81 days.

(21) Appl. No.: 14/358,742

(22) PCT Filed: Nov. 9, 2012

(86) PCT No.: PCT/IB2012/056280  
§ 371 (c)(1),  
(2) Date: May 16, 2014

(87) PCT Pub. No.: WO2013/072823  
PCT Pub. Date: May 23, 2013

(65) Prior Publication Data  
US 2014/0378871 A1    Dec. 25, 2014

Related U.S. Application Data

(60) Provisional application No. 61/560,905, filed on Nov. 17, 2011.

(51) Int. Cl.  
*A61B 5/117* (2006.01)  
*A61B 5/103* (2006.01)  
(Continued)

(52) U.S. Cl.  
CPC .............. *A61M 16/06* (2013.01); *A61B 5/1077* (2013.01); *A61B 5/1078* (2013.01);  
(Continued)

(58) Field of Classification Search  
CPC .................................... G01B 7/18; G01B 7/28  
USPC ....... 600/587; 33/511, 512; 73/172; 702/150, 702/152, 155, 156; 434/262, 267  
See application file for complete search history.

(56) References Cited

U.S. PATENT DOCUMENTS 5,459,329 A    10/1995  Sinclair  
6,127,672 A    10/2000  Danisch  
(Continued)

FOREIGN PATENT DOCUMENTS

FR    2906025    3/2008  
JP    2004150886    5/2004

OTHER PUBLICATIONS

Chouaf et al, "Stress Analysis at Singular Points of Micromachined Silicon Membranes", Sensors and Actuators, vol. 84, 2000, p. 109-115.

*Primary Examiner* — Brian Szmal  
(74) *Attorney, Agent, or Firm* — Michael W. Haas

(57) ABSTRACT

A device (10) for capturing a surface of an object (30) is provided, wherein the device (10) comprises a flexible membrane (14), which is configured to be deformed from a first shape to a second shape, when at least a part of the flexible membrane (14) is brought into contact with the surface of the object (30), wherein the device (10) comprises a plurality of strain-gauges (18) coupled to the flexible membrane (14), wherein the strain-gauges (18) are configured to measure a plurality of strain signals that depend on the shape of the flexible membrane (14), and wherein the device (10) comprises an output unit (24) for outputting the strain signals for reconstruction of the surface of the object (30) as a function of the strain signals.

10 Claims, 3 Drawing Sheets

(51) Int. Cl.
 *A61M 16/06* (2006.01)
 *G01B 7/16* (2006.01)
 *G01B 7/28* (2006.01)
 *A61B 5/107* (2006.01)
 *A61B 5/00* (2006.01)

(52) U.S. Cl.
 CPC ............... *A61B 5/6814* (2013.01); *G01B 7/18* (2013.01); *G01B 7/28* (2013.01); *A61B 2562/0261* (2013.01); *A61B 2562/046* (2013.01); *A61M 2016/0661* (2013.01); *A61M 2205/50* (2013.01); *A61M 2207/00* (2013.01); *Y10T 29/49* (2015.01)

(56) References Cited

U.S. PATENT DOCUMENTS

| | | | |
|---|---|---|---|
| 6,753,131 | B1 | 6/2004 | Rogers et al. |
| 7,881,916 | B1 | 2/2011 | Saisan |
| 2003/0139896 | A1 | 7/2003 | Dietz et al. |
| 2004/0206365 | A1 | 10/2004 | Knowlton |

DEVICE AND METHOD FOR CAPTURING A SURFACE OF AN OBJECT

CROSS-REFERENCE TO PRIOR APPLICATIONS

This application is the U.S. National Phase application under 35 U.S.C. §371 of International Application Serial No. PCT/IB2012/056280, filed on Nov. 9, 2012, which claims the benefit of U.S. Application Ser. No. 61/560,905, filed on Nov. 17, 2011. These applications are hereby incorporated by reference herein.

FIELD OF THE INVENTION

The present invention relates to a device and a method for capturing a surface of an object, in particular for capturing a 3D contour, such as a facial geometry.

BACKGROUND OF THE INVENTION

Facial contour and geometry are being used to design masks and to identify mask usage in many medical fields including CPAP (constant positive air pressure). CPAP masks are used to provide a breathable mixture of gases, typically air, provided at above ambient pressure to a patient. A CPAP mask forms a seal around a nose and mouth of a patient's face, providing an interface between the air source and the patient's respiratory system that is ideally free of leaks. CPAP masks are used in a wide variety of medical treatment procedures.

A CPAP mask comprises a dome and a cuff, which forms a seal around the patient's face. The dome fits over the patient's nose and mouth, and provides a conduit to the source of air. Ideally, the seal is air-tight under the pressure in normal service. Typically, cuffs in CPAP masks comprise silicone gaskets, and other materials with similar properties of high elasticity. The problem which the cuffs in CPAP masks often lead to is irritation around the face of the patient. This is particularly found in medical environments, where the masks may be worn for hours or days without changing or removing from the face. This occurs because silicone gaskets often do not seal well to the patient's face, especially around the bridge and lower sides of the nose. The resulting air leaks into the patient's eyes, causing eye irritation. These air leaks can be avoided by pushing the CPAP mask more tightly to the patient's face. However this pressure can lead to minor red marks or open sores. Additionally, individuals have widely varying sensitivities to mechanical pressure. A combination of skin and eye irritation reduces patient tolerance and compliance with the medical procedure utilizing the mask.

CPAP masks often will not acceptably seal to a face with wrinkles or other irregularities, as it is often found in older persons that commonly employ CPAP procedures. In order to maximize compliance for the CPAP therapy, the CPAP masks have to be customized and to be adjusted as well as possible to the patient's face. Therefore the facial contour and geometry of the patient's face has to be captured for customizing the CPAP masks. There have been many attempts to capture such data digitally with non-contact methods, such like digital scans. However, the known methods run into the issue of facial hairs, deep lines and wrinkles, which create noises to the 3D digital models. These noises prevent to accurately identify the landmarks of the object to be measured.

SUMMARY OF THE INVENTION

Accordingly, it is an object of the present invention to provide a device and a method that overcomes the shortcomings of the conventional mask fitting devices and methods.

In a first aspect of the present invention a device is presented that captures a surface of an object, wherein the device comprises a flexible membrane, which is configured to be deformed from a first shape to a second shape, when at least a part of the flexible membrane is brought into contact with the surface of the object, wherein the device comprises a plurality of strain-gauges coupled to the flexible membrane, wherein the strain-gauges are configured to measure a plurality of strain signals that depend on the shape of the flexible membrane, and wherein the device comprises an output unit for outputting the strain signal for reconstruction of the surface of the object as a function of the strain signals.

In a further aspect of the present invention an arrangement for reconstructing a surface of an object is presented, which comprises a device according to the present invention for providing a plurality of strain signals, and which comprises a processing unit coupled to the device for reconstructing the surface of the object as a function of the strain signals.

In a further aspect of the present invention a method for capturing a surface of an object by means of flexible membrane that is coupled with a plurality of strain-gauges is presented, wherein the method comprises bringing at least a part of the flexible membrane into contact with the surface of the object, wherein the flexible membrane is deformed from a first shape to a second shape, wherein the method comprises measuring a plurality of strain signals by means of the strain-gauges, wherein the strain signals depend on the shape of the flexible membrane, and wherein the method comprises reconstructing the surface of the object as a function of the strain signals.

When applying the device according to the present invention, the flexible membrane is wrapped over the patient's face. As a result of this, the flexible membrane is deformed to create a close replica of the facial contour. Due to the good elasticity of the material of the membrane a very smooth representation of the patient's face is achieved. The elasticity substantially prevents any disturbing noises, such like facial hairs, deep lines and wrinkles The facial hair for example, is compressed by bringing the flexible membrane into contact with the patient's face. This minimizes the noise, respectively the error of the representation of the patient's face. The result is a smooth contour, ready for mask formation or identification. In summary, the device and method according to the present invention provide a very easy way to capture a very smooth and close representation of a patient's face without the need to apply complex computer modeling. The resolution of the captured facial contour depends on the number of strain-gauges that are applied by the device according to the present invention.

Preferred embodiments of the invention are defined in the dependent claims.

In a first embodiment, the first shape of the flexible membrane substantially conforms to a plane.

During this condition of the device, the strain-gauges can be exactly calibrated for the further usage.

In another embodiment the flexible membrane is held by a rigid frame.

The rigid frame is used to accommodate the forces that are applied to the flexible membrane, when bringing the flexible membrane into contact with the surface of the object. Additionally, the rigid frame can keep the output unit for outputting the strain signals. The rigid frame can even hold a processing unit and/or a storage unit for reconstructing the surface of the patient's face as a function of the strain signals. The storage unit is e.g. used for storing the measured strain signals and the results of the processing unit.

In a further embodiment the flexible membrane is mechanically coupled with the rigid frame by means of strain-gauges, which are arranged all around a peripheral part of the flexible membrane.

In this embodiment one part of the strain-gauges is mechanically coupled with an edge of the flexible membrane, whereas the other part of the strain-gauges is mechanically coupled to the rigid frame. So the strain-gauges fulfill two functionalities. On one hand the strain-gauges measure the strain signals that are caused by the deformation of the flexible membrane, and on the other hand the strain-gauges are used to mechanically couple the flexible membrane with the rigid frame. The number of the strain-gauges that are applied to this embodiment influence the mechanical stability of the device and the resolution of the captured facial contour.

In another embodiment the strain-gauges are mounted on a surface of the flexible membrane or the strain-gauges are arranged within the flexible membrane.

In this embodiment the strain-gauges are distributed all over the flexible membrane in order to capture a detailed representation of the patient's face. The strain-gauges can either be mounted on a surface of the flexible membrane or they can be arranged within the flexible material of the membrane. It is also possible to arrange a higher number of strain-gauges in critical regions, where it is difficult to capture a facial geometry (e.g. region that is attached to the bridge).

In a further embodiment the flexible membrane is made of a flexible material, in particular silicone or elastomer.

The flexible membrane allows on one hand to smoothen facial irregularities like facial hairs, deep lines and wrinkles in order to avoid any disturbing noises in the 3D representation of the patient's face. On the other hand the flexible membrane has to hold the strain-gauges, which are used to measure the strain signals. When the flexible membrane is brought into contact with the patient's face, the tension of the flexible membrane has to be carefully calibrated, so that it is very similar to the tension that is applied by the CPAP mask. This calibration assures a correct representation of the patient's face when wearing a CPAP mask.

It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
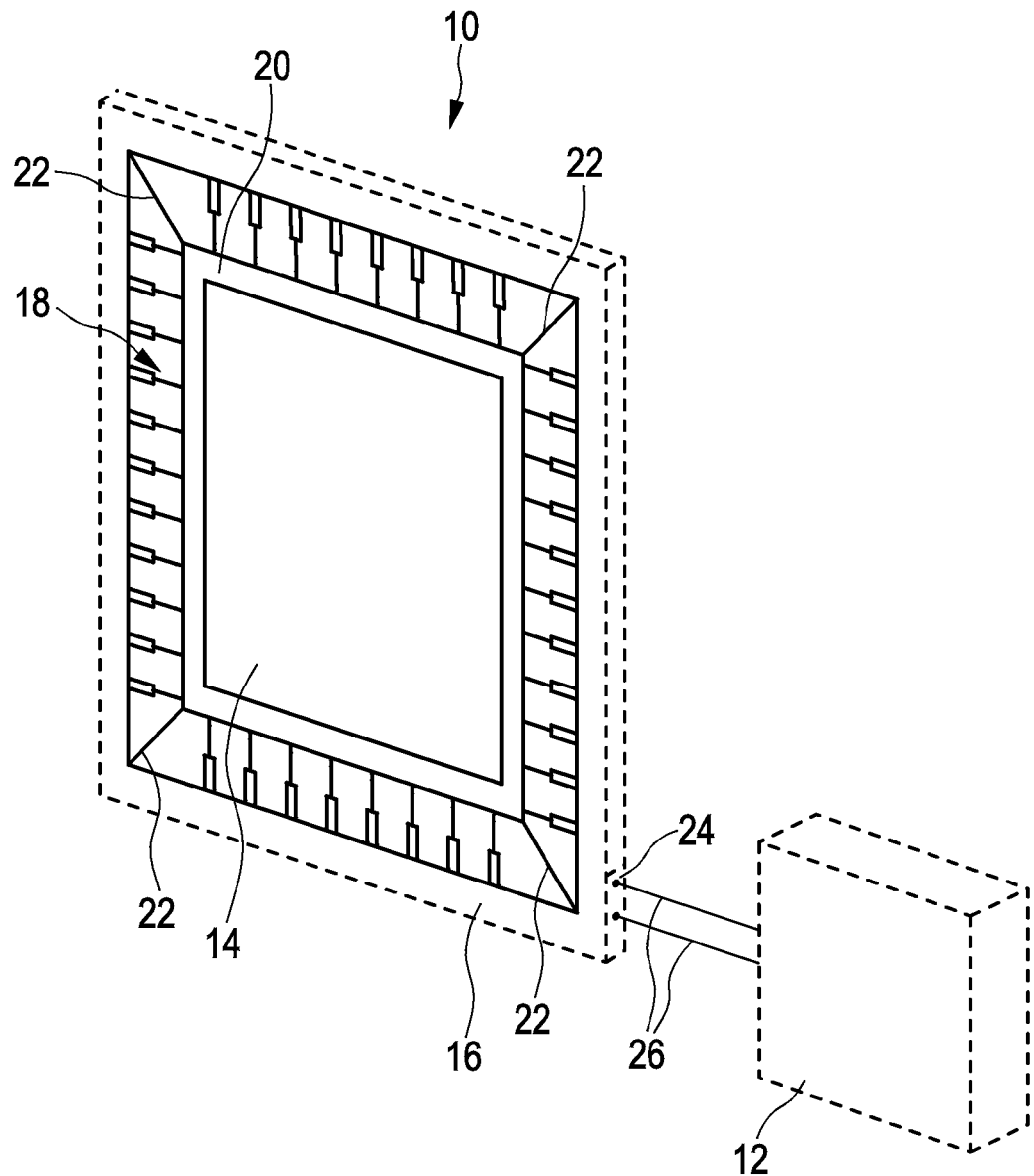
FIG. 1 shows a preferred embodiment of the disclosed device, coupled to a processing unit for reconstructing the surface of the object.

FIG. 1 illustrates a device 10 for capturing a facial contour, which is electrically coupled to a processing unit 12. The device 10 comprises a flexible membrane 14, which is held by a rigid frame 16 by means of a plurality of strain-gauges 18. The flexible membrane 14 is made of a soft and thin silicone or any other elastomer. The strain-gauges 18 are arranged all around the flexible membrane 14, wherein one contact of each of the strain-gauges 18 is mounted on a peripheral part 20 of the flexible membrane 14 and wherein the other contact of each of the strain-gauges 18 is coupled to the rigid frame 16. Additionally, the flexible membrane 14 is mechanically supported by straps 22, which connect the flexible membrane 14 with the rigid frame 16. Furthermore, the device 10 comprises an output unit 24, which electrically connects the device 10 to the processing unit 12. In this embodiment the output unit 24 is coupled to the processing unit 12 via electric cables 26.

In an alternative embodiment, the connection between the output unit 24 and the processing unit 12 can also be realized via a wireless network. Alternatively, the processing unit 12 can also be arranged within the rigid frame 16 of the device 10.

In a further alternative embodiment the strain-gauges 18 can also be mounted on any place of the surface of the flexible membrane 14. Furthermore, the strain-gauges 18 can also be arranged within the flexible material of the flexible membrane 14. Additionally, the number of the strain-gauges 18 can be higher in critical regions, where it is difficult to capture the 3D facial contour (e.g. regions that are likely to be attached to the bridge and lower sides of the nose). More strain-gauges 18 can for example be positioned in a region that is brought into contact with the nose of the human's face, whereas less strain-gauges 18 are applied in a region that is brought into contact with the cheeks of the human's face. In general, the resolution of the captured 3D facial contour depends on the number of strain-gauges 18 that are applied within the device 10.

Figure 2:
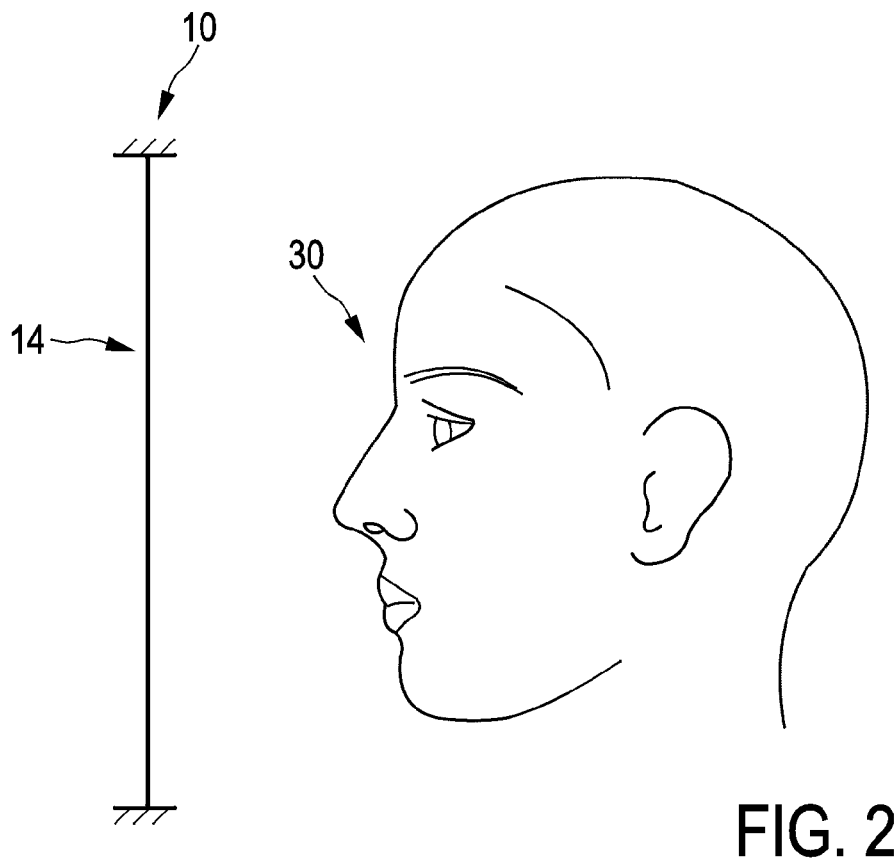
FIG. 2 shows a perspective view of the disclosed device and a patient's face in an initial condition.

FIG. 2 shows a perspective view of the disclosed device 10 and a patient's face 30 in an initial condition. During this status the flexible membrane 14 substantially conforms to a plane and forms a first shape. The strain-gauges 18, which are not shown in FIG. 2 due to the schematic view of the device 10, are calibrated in such a way, so that the measured strain signals will not indicate any deformation of the flexible membrane 14.

Figure 3:
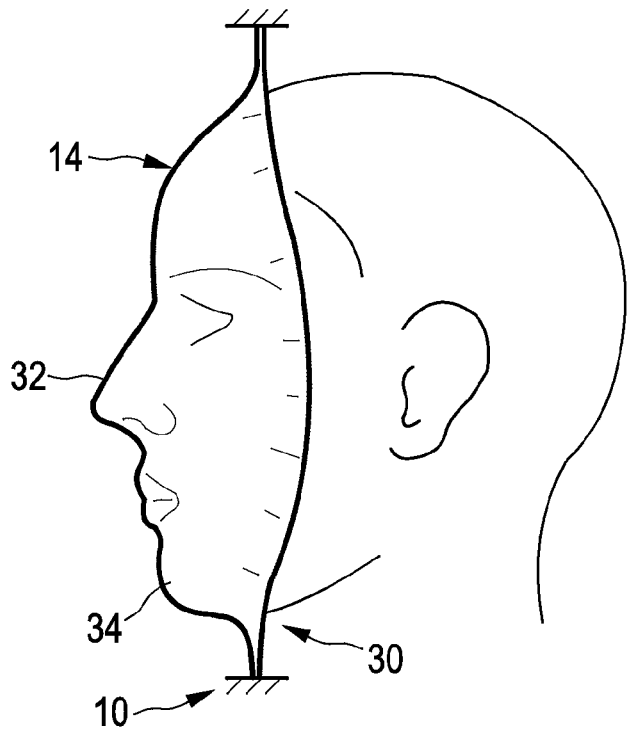
FIG. 3 shows a perspective view of the disclosed device and the patient's face in a second condition, when the device is applied to the patient's face.

In order to capture the 3D information about the patient's face 30, the device 10, respectively the membrane 14 is brought into contact with the patient's face 30. In this condition, which is shown in FIG. 3, the flexible membrane 14 conforms to the patient's face 30 and forms a second shape. The forces caused by bringing the flexible membrane 14 into contact with the patient's face 30 are accommodated by the strain-gauges 18 and the straps 22. The strain-gauges 18 and the straps 22 are not shown in FIG. 3 due to the schematic view of the device 10. The tension of the flexible membrane 14 must be carefully calibrated, so that it equals the tension that would have been applied by a CPAP mask. This is necessary to assure that a correct representation of the patient's face 30 is captured by the device 10. By attaching, respectively pulling the flexible membrane 14 on the patient's face 30 facial hairs are compressed and deep lines, respectively wrinkles of the patient's face 30 are substantially removed. As a result, a very smooth representation of the patient's face 30 can be captured. Due to the deformation of the flexible membrane 14 from the first shape to the second shape, a plurality of strain signals is measured by the strain-gauges 18. The measured strain signals depend on the shape/deformation of the flexible membrane 14. So in the nose region 32, a larger strain signal is measured as for example in the chin region 34. The measured strain signals are then transmitted via the electric cables 26 to the processing unit 12. Alternatively, the strain signals can also be transmitted via a wireless network to the processing unit 12. The processing unit 12 can for example be a PC or a Smartphone. Finally, the 3D facial contour of the patient's face 30 is reconstructed on the PC as a function of the measured strain signals.

Figure 4:
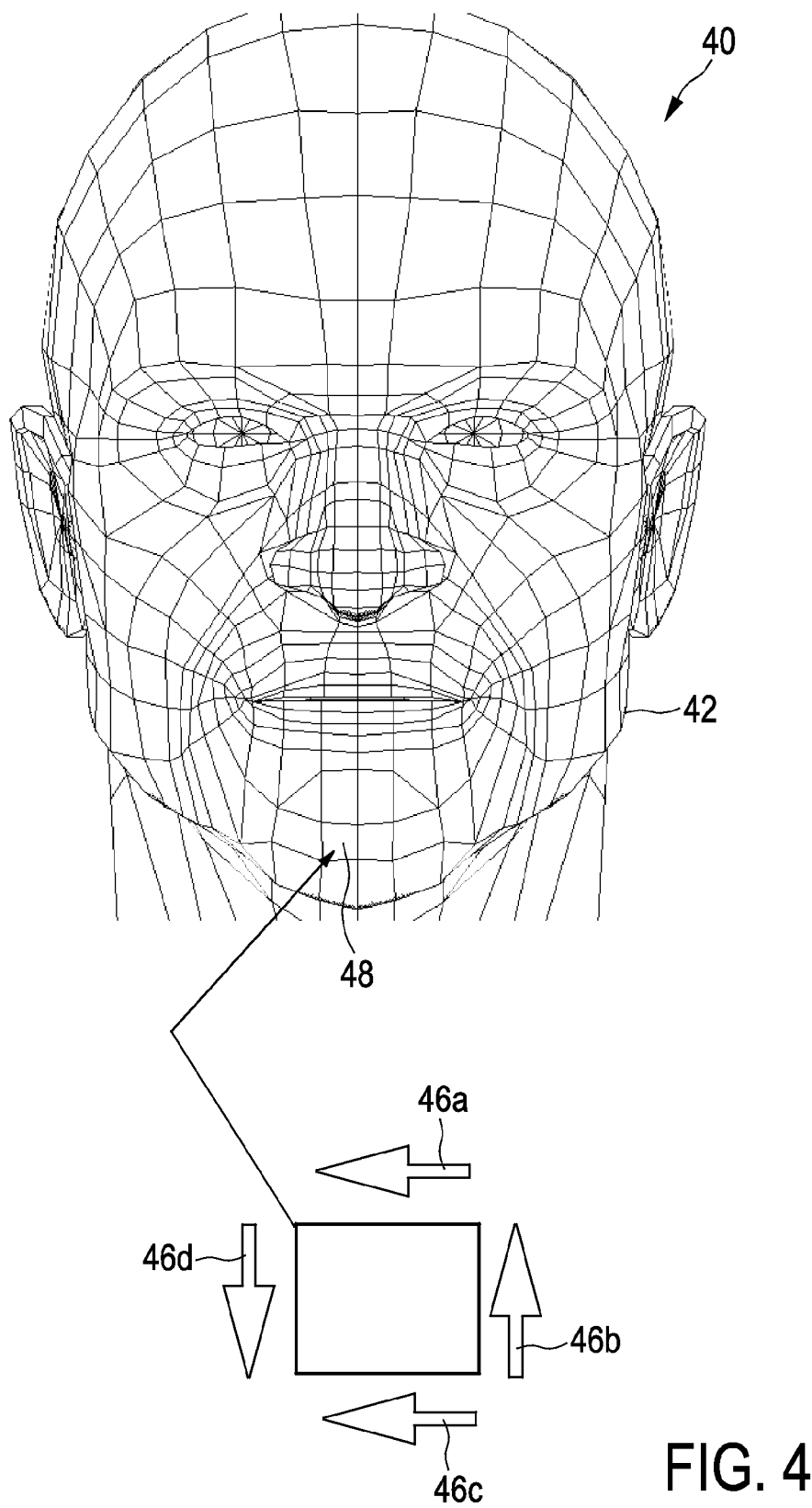
FIG. 4 shows a 3D-representation of the patient's face.

FIG. 4 shows an exemplary 3-D representation 40 of the patient's face 30. The 3-D representation 40 results from the reconstruction process running on the processing unit 12. The 3-D representation 40 is based on a mesh model 42, which correlates to a grid system that is built by a corresponding arrangement of the strain gauges 18 on the flexible membrane 14. When the flexible membrane 14 is pulled on the patient's face 30, the strain gauges 18 measure the deformation of the flexible membrane 14. This is shown in FIG. 4 by means of an exemplary grid section 44. The strain gauges 18 measure forces 46 along the grid section 44. The forces 46 are then translated into a respective deformation of a corresponding mesh section 48. The relationship between the measured forces 46 and the respective deformation of the corresponding mesh section 48 is calculated based on the properties and the thickness of the material of the flexible membrane 14. The calculation can be done by using a mathematical model. The translation of the forces 46 can also be achieved via a 3-D CAD software. Finally, by combining all mesh sections 48, the 3-D representation 40 of the patient's face 30 is formed.

The reconstructed 3D facial contour can then be used to customize the design of CPAP masks (or any other masks) or it can be used in a mask identification program. By means of the captured facial contour and the resulting representation of the patient's face the fit of a mask can be significantly improved. This results in a higher comfort when wearing the mask and in a higher acceptance for the therapy. The risk for pressure points, red marks or even wounds can be significantly reduced.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In particular, it is not intended to limit the scope of the invention to the design of CPAP masks. The device and method according to the invention can be used for the design of any mask worn by a person.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for capturing a surface of an object comprising:
    a flexible membrane, which is configured to be deformed from a first shape to a second shape, when at least a part of the flexible membrane is brought into contact with the surface of the object, wherein the flexible membrane is held by a rigid frame;
    a plurality of strain-gauges coupled to the flexible membrane, wherein the strain-gauges are configured to measure a plurality of strain signals that depend on the shape of the flexible membrane; and
    an output unit for outputting the strain signals for reconstruction of the surface of the object as a function of the strain signals.

2. The device according to claim 1, wherein the first shape conforms to a plane.

3. The device according to claim 1, wherein the flexible membrane is mechanically coupled with the rigid frame by means of the strain-gauges, which are arranged all around a peripheral part of the flexible membrane.

4. The device according to claim 1, wherein the strain-gauges are mounted on a surface of the flexible membrane or wherein the strain-gauges are arranged within the flexible membrane.

5. The device according to claim 1, wherein the flexible membrane is made of silicone or an elastomer.

6. An arrangement for reconstructing a surface of an object comprising:
    a device according to claim 1 for providing a plurality of strain signals; and
    a processing unit coupled to the device for reconstructing the surface of the object as a function of the strain signals.

7. A method of providing a mask for a patient, including using the device according to claim 1 to generate 3D information of the pantient's face, using the 3D information of the patient's face for (i) manufacturing the mask for the patient, (ii) determining the shape of the mask for the patient and/or (iii) selecting the mask suitable for the patient from a predetermined set of masks.

8. A method for capturing a surface of an object by means of a flexible membrane that is coupled with a plurality of strain-gauges, the method comprising:
    bringing at least a part of the flexible membrane into contact with the surface of the object, wherein the flexible membrane is deformed from a first shape to a second shape, wherein the flexible membrane is held by a rigid frame;
    measuring a plurality of strain signals by means of the strain-gauges, wherein the strain signals depend on the shape of the flexible membrane; and
    reconstructing the surface of the object as a function of the strain signals.

9. The method according to claim 8, wherein the first shape conforms to a plane and wherein the second shape conforms to the surface of the object (30).

10. A method of providing a mask for a patient, including receiving 3D information of the patient's face by means of the method according to claim 8, and customizing a design of the mask for the patient based on the 3D information or identifying the mask in a mask identification program using the 3D information.

* * * * *